United States Patent [19]

Moussebois et al.

[11] 4,397,960
[45] Aug. 9, 1983

[54] IMMUNOASSAYS USING F(AB')2 FRAGMENTS

[75] Inventors: Claude H. Moussebois; Pierre L. Masson, both of Brussels; Jean-Pierre Vaerman, Wavre; Joseph Limet, Marchin; Cesar L. Cambiaso, Kraainem, all of Belgium

[73] Assignee: Technicon Instruments Corporation, Tarrytown, N.Y.

[21] Appl. No.: 362,334

[22] Filed: Mar. 26, 1982

Related U.S. Application Data

[63] Continuation of Ser. No. 5,261, Jan. 22, 1979, abandoned.

[30] Foreign Application Priority Data

Jan. 26, 1978 [GB] United Kingdom ................. 3237/78

[51] Int. Cl.$^3$ ............................................ G01N 33/54
[52] U.S. Cl. .................................... 436/512; 436/509; 436/526; 436/533; 436/534
[58] Field of Search ........................ 23/230 B; 424/12; 436/512, 526, 534, 509

[56] References Cited

U.S. PATENT DOCUMENTS

| | | | |
|---|---|---|---|
| Re. 29,474 | 11/1977 | Axen | 424/1 |
| 3,646,346 | 2/1972 | Catt | 23/230 B |
| 4,115,534 | 9/1978 | Ithakissios | 23/230 B |
| 4,200,436 | 4/1980 | Mochida | 23/230 B |
| 4,253,844 | 3/1981 | Limet | 436/512 |

Primary Examiner—Sidney Marantz
Attorney, Agent, or Firm—S. P. Tedesco

[57] ABSTRACT

Immunoassays for antigens or haptens are effected using, instead of an immunoglobulin antibody, the F(ab')$_2$ fragments thereof. In this way, interference from endogenous RF and Clq in the fluid under assay is avoided without the necessity of pre-treating the fluid to remove or inactivate the RF or Clq. The assays may be of various types including latex agglutination and competitive binding assays. A reagent for such use comprising F(ab')$_2$ fragments insolubilized on a water-insoluble substrate, especially a particulate substrate, is described.

13 Claims, No Drawings

IMMUNOASSAYS USING F(AB')2 FRAGMENTS

This is a continuation of application Ser. No. 005,261, now abandoned filed Jan. 22, 1979.

This invention is concerned with immunoassays, more particularly with immunoassays involving the binding properties of immunoglobulins, and with certain reagents useful in such assays.

It is well known that antibodies will bind with the corresponding specific antigens or haptens (Ag), and use is made of this in many immunoassay procedures. For example, human sera can be assayed for the presence therein of a particular Ag by using a corresponding antibody, for example by competitive binding techniques or latex agglutination techniques. These and other techniques are well known in the art.

One problem which can arise in such immunoassay procedures is interference by other proteins present in the serum under assay. In particular, human serum contains rheumatoid factor (RF) and Clq (a component of complement), and both these substances bind with IgG antibodies. Moreover, the amounts of RF and Clq in human sera can vary widely and it is usually necessary, therefore, to treat the sera (prior to said assay) to inactivate or remove endogenous RF and Clq. If this is not done, the assay results (particularly any quantitative results) may be significantly in error.

We have now devised a method of immunoassay involving the binding property of antibodies for antigens (by which term we include haptens), which can be carried out in the presence of RF and/or Clq without interference therefrom. In particular, according to the present invention, the method of immunoassay utilises the F(ab')2 fragments of the immunoglobulin rather than whole immunoglobulin. The F(ab')2 fragments of, for example, IgG have the property of specific binding with antigen, but they do not bind with RF or Clq. (The F(c) fragment of IgG is responsible for the binding reaction of IgG with RF or Clq, but not for the binding reaction with a specific antigen.) It will be appreciated that by proceeding according to the method of the invention, the specificity of the immunoglobulin towards a particular Ag is maintained, but without the associated property of binding with RF and/or Clq.

The invention thus provides a method of immunoassay which comprises reacting an antigen in a fluid with the F(ab')2 fragments of an immunoglobulin which is specific to said antigen, the reaction being effected in the substantial absence of the (whole) immunoglobulin and of F(c) fragments thereof.

The invention also provides a method of assaying a fluid for the presence and/or amount therein of an antigen, which comprises the steps of:

(a) mixing a sample of the fluid with the F(ab')2 fragments of an immunoglobulin which is specific to said antigen, to form a reaction mixture, the reaction mixture being substantially free from the whole immunoglobulin and the F(c) fragments thereof;

(b) incubating the mixture to allow reaction between the said F(ab')2 fragments and any said antigen present, and (c) determining the extent (if any) to which said reaction has occurred in the mixture and thereby the presence and/or amount of said antigen in said fluid sample.

Immunoglobulins such as IgG can be split into their constituent F(ab')2 and F(c) fragments by methods known in the art, for example by enzymatic digestion using pepsin. The F(ab')2 fragments can then be separated from the F(c) fragments and used in the method of the invention. One example of the preparation of F(ab')2 is as follows. Whole IgG is mixed with pepsin (2 mg pepsin per 100 mg IgG) in a 0.1 M acetate buffer of pH 4.5. The mixture is incubated for 24 hours at 37° C. The F(ab')2 formed is then separated on an Ultrogel AcA 4.4 column, yielding 80–90% of the theoretical yield of F(ab')2.

The F(ab')2 immunoglobulin fragments can be used in place of whole immunoglobulin in accordance with the invention in a variety of immunoassay procedures in which a specific reaction occurs between the immunoglobulin and an antigen, but in which no reaction is required between the immunoglobulin and RF or Clq. (It will be appreciated that there are known assays in which RF and Clq is added as a reagent to react with an immunoglobulin. The F(ab')2 fragments cannot be used simply as replacements for whole immunoglobulin in such assays.) Thus, the F(ab')2 fragments may be used in solution, in for example, certain competitive binding assays. It is often advantageous to use a radioactive atom or other label in such assays (and other assays) and the F(ab')2 fragments may carry such a label, the extent of reaction between the antigen and the fragments then being determined utilising the label. In one example of a competitive binding assay of the invention, the antigen-containing fluid is mixed with both labelled and unlabelled F(ab')2 fragments whereby a competitive binding reaction occurs between the said fragments and the said antigen; and wherein the amount of labelled fragments which either have reacted with the antigen or remain unreacted in the mixture, is analysed whereby the presence and/or amount of antigen in the fluid is determined.

The F(ab')2 fragments may be used in insolubilised form, i.e. bound (by which we include both absorbed and covalently linked) to a water-insoluble substrate. The nature of the substrate can vary widely: for example it may be in sheet form, or in the form of a hollow tube, or it may be a particulate material. One preferred form or particulate material is magnetically attractable so that, after reaction between the antigen under assay and the fragments, the particulate material may be separated by using a magnetic field. Assays of this type are described in our Belgian Pat. no. 852327 to which reference should be made for further details.

Another preferred form of insolubilised F(ab')2 fragments is a latex suspension, and such suspensions can be used in place of whole immunoglobulin in latex agglutination tests for antigens. In such tests, a sample of the fluid to be tested for an antigen (for example human serum) is mixed with latex particles which have a coating of an antibody to the said antigen. In the method of the invention, F(ab')2 fragments are used in place of whole antibody in the coating. Specific binding between the coating and the antigen causes the latex particles to become agglutinated. The extent of agglutination can be observed visually (for qualitative results) or can be quantitated by counting (preferably by automatic counting of the agglutinated, or more preferably the unaggltutinated particles).

In another aspect, therefore, the invention includes a method of quantitatively assaying an Ag in a fluid, wherein a sample of the fluid under assay is mixed with latex particles having said F(ab')$_2$ fragments bound thereto, to form a reaction mixture, reaction between said antigen and said F(ab')$_2$ fragments causing agglutination of the latex; and wherein the mixture is observed to determine the extent (if any) of agglutination whereby the presence and/or amount of the said antigen in said fluid sample is determined.

It should be noted that, in latex agglutination tests using F(ab')$_2$ fragments, there should not be any dithiothreitol (DTT) present since this inhibits agglutination. Any DTT can be inactivated by oxidation with hydrogen peroxide.

The method of assay of the invention may, in appropriate cases be effected by continuous flow techniques (which are known in the art) in which individual segments of reaction mixture are passed along the conduit, separated by an inert segment (e.g. air) and, if desired a wash liquid segment. This is described in U.S. Pat. No. 2,797,149 to which reference should be made for further details.

Insolubilised F(ab')$_2$ fragments can be prepared in a number of ways. The fragments may, for example, be absorbed onto a suitable substrate surface. Alternatively, whole immunoglobulin (e.g. IgG) can be covalently bound to a substrate surface and then treated to split off the F(c) fragments, leaving the F(ab')$_2$ fragments covalently linked to the substrate. Thus, F(ab')$_2$ coated latex can be produced in either of these ways, i.e. the latex (having an absorptive coating thereon) can be mixed with F(ab')$_2$ fragments in a buffer, whereupon the F(ab')$_2$ fragments are absorbed directly on to the latex, or whole antibody can be coupled to the latex and then split to release the F(c) fragments (which can then be removed from the mixture), leaving the F(ab')$_2$ fragments bound to the latex. In one example of this procedure, IgG is bound to latex by the method described in our copending U.K. application No. 3238/78 (Case 2090F) to which reference should be made for full details. Briefly, the method comprises first coating the latex with a protein which sticks strongly to the latex and is relatively resistant to proteolysis. An example of such a protein is lactoferrin. The antibodies are then covalently coupled to the lactoferrin using, for example, the Leuchs anhydride of N-$\epsilon$-chloroacetyl lysine (NCA) as the coupling agent. The latex-lactoferrin-NCA-antibodies are then digested with pepsin, for example under the following conditions: 0.2 M acetate buffer, pH 3.2, pepsin immunoglobulin ratio=1/10, 0.5% latex suspension, incubation for 60 minutes at 37° C. There is thus obtained latex particles carrying the F(ab')$_2$ fragment of the immunoglobulin.

The latex particles (or other F(ab')$_2$-bearing substrates) obtained in this way, and by the absorbtion method, are not agglutinated by RF levels such as occur in sera rich in RF. The latex particles can be successfully used in the latex agglutination tests for Ag, even in the presence of RF or Clq.

The invention also provides a reagent for use in immunoassay which comprises a suspension of finely divided particulate material having bound thereto the F(ab')$_2$ fragments of an immunoglobulin, the suspension being substantially free from the said immunglobulin and F(c) fragments thereof. In such reagents, the F(ab')$_2$ fragments may for example, be covalently bound or absorbed on the particles. The particles may comprise magnetically attractable material and the fragments may carry an identifying label. The particles may be of any convenient size but generally they will be from about 1 to 30$\mu$. Especially (but not only) in the case of use in continuous flow techniques, the specific gravity of the particles should be from about 1.4 to 3.2 to avoid undue floating or settling of the particles in the reaction mixture.

In order that the invention may be more fully understood, the following Examples are given by way of illustration only.

EXAMPLE 1

Preparation of F(ab')$_2$ latex particles by absorbtion

A 10% suspension of latex particles (Dow, 0.794 micron diameter, S.D. 0.44 micron, No. 41943, Serva Feinbiochemica, D-6900 Heidelberg 1, Germany) is diluted 20 times with 0.02 M glycine/0.035 M NaCl buffer, pH 9.1, and washed once with this buffer. 1/10th Volume of F(ab')$_2$ solution, 2 to 3 mg per ml., prepared as above, is added and after 10 to 15 minutes incubation at room temperature, 1/10th volume of 10% human serum albumin (HSA), in the same buffer as the latex, is added to ensure saturation with protein. After a further 20 to 30 minutes incubation, the latex is washed twice with the original buffer before re-suspending in the original volume of 0.10 M glycine/0.17 M NaCl buffer, pH 9.1, containing 1% HSA, to give a latex suspension of 0.5% (i.e. diluted 20 times compared to the original concentration).

Antiserum

Antiserum to IgE was raised in rabbits using Freund's complete adjuvant and diluted 10 times in clycine buffer containing 3 drops "Tween 20" per liter, and filtered through 0.22 micron Milipore (GWSP 06700) filter before use.

Automated Assay

Patients serum was aspirated at the rate of 0.1 ml. per minute into a continuous flow system comprising a peristaltic pump, manifold, particle counter and recorder. The serum was mixed with 1.0 ml. of glycine buffered latex particles and passed through an incubation coil for 10 minutes. The solution then flowed into a cell counter where the unagglutinated particles were counted, the agglutinated particles being electronically screened out. The concentration of IgE in the serum was directly proportional to the decrease in particles in the range 6 to 100 IU (international units) of IgE. Thirteen patients' samples run repeatedly showed a coefficient of variation of 2% at mid-range and a correlation coefficient of 0.95 when compared with a radioimmunossay test.

EXAMPLE 2

Preparation of F(ab')$_2$ covalently linked to latex 12 mg N-$\epsilon$-chloroacetyl lysine N-carboxy-anhydride (NCA), dissolved in 100 $\mu$l dioxane, was added to 50 mg iron-saturated lactoferrin in 1 ml phosphate buffered saline, pH 7.2 (PBS). After incubation for 24 hours in the dark at 4° C., the preparation was lyophilised for storage. Polystyrene latex particles (0.8$\mu$ diameter, 10% suspension) were coated by mixing 500 $\mu$g of NCA-lactoferrin with 0.4 ml of PBS and 50 $\mu$l of 10% latex. After 45 min incubation at room temperature, the particles were twice washed with 1 ml of 0.2 M carbonate buffer, pH 9.6. To avoid hydrolysis of the chloroacetyl groups at alkaline pH, reduced IgG Ab had to be added immediately. IgG was prepared from rabbit anti-horse spleen ferritin by ammonium sulphate precipitation followed by DEAE-cellulose chromatography. The IgG, at a final concentration of 8 mg/ml in 0.1 M phosphate solution, pH 8.5, was reduced for 1 hour at 37° C. with 1.1 mM dithiothreitol (DTT). Mixtures comprising 1 ml of the 0.5% suspension of freshly prepared NCA-lactoferrin-latex and various volumes (15 μl to 125 μl) of reduced IgG Ab solution were deoxygenated by bubbling nitrogen through for a few seconds; the tube was then sealed under vacuum. After 24 hours at room temperature in the dark, the latex was washed twice with 0.4 M carbonate buffer pH 9.6 containing 1% BSA and 0.1% Tween-20 and resuspended in GBS-BSA. Non-covalently bound IgG was removed with Tween-20. To digest the Ab (IgG) coupled to the protein interface, the particles were suspended in 0.1 M acetate buffer, pH 3.2, and incubated for 1 hour at 37° C. with pepsin at an enzyme/substrate ratio of 1/10 (w/w). After centrifugation and twice washing the particles with 0.1 M glycine-HCl buffer, pH 9.2, containing 0.17 M NaCl (GBS) and 1% bovine serum albumin (BSA) (GBS-BSA), the presence of intact IgG on the particles was checked by measuring agglutination with rheumatoid sera, and latex preparations reacting with rheumatoid sera were again digested with pepsin until no such further agglutination was observed. Latex agglutination tests for ferritin in serum were carried out as in Example 1 using the above reagent, with very satisfactory results.

We claim:

1. A method of immunoassay which comprises reacting an antigen in a fluid with insolubilized F(ab')$_2$ fragments of an immunoglobulin which is specific to said antigen, the reaction being effected in the substantial absence of the (whole) immunoglobulin and of F(c) fragments thereof.

2. A method of assaying a fluid by agglutination for an antigen therein, which comprises the steps of:
   (a) mixing a sample of the fluid with F(ab')$_2$ fragments of an immunoglobulin which is specific to said antigen to form a reaction mixture, said fragments being bound to water-insoluble particles, wherein, to avoid interference from exogenous C1q and RF, the reaction mixture is substantially free from the whole immunoglobulin and the F(c) fragments thereof;
   (b) incubating the mixture to allow reaction between the said F(ab')$_2$ fragments and any said antigen present to cause agglutination of said particles; and
   (c) directly determining the extent to which agglutination of said particles has occurred in the mixture and thereby the presence and/or amount of said antigen in the fluid sample.

3. A method according to claim 2, wherein said particles are latex particles.

4. A method according to claim 2, wherein the extent of agglutination is determined by selectively counting the agglutinated or unagglutinated latex particles.

5. A method according to claim 2, wherein said particles are magnetically attractable and wherein, after reaction between the antigen and the fragments, the particulate material is separated by using a magnetic field.

6. A method according to claim 2, wherein the fluid under assay is a biological fluid.

7. A method according to claim 2, wherein the fluid under assay is human serum.

8. A method according to claim 2, which is effected by continuous flow techniques.

9. A method according to claim 2, which is effected by a discrete manual technique.

10. A reagent for use in immunoassay which comprises a suspension of finely divided particulate material having bound thereto the F(ab')$_2$ fragments of an immunoglobulin, the suspension being substantially free from the said whole immunoglobulin and F(c) fragments thereof.

11. A reagent according to claim 10 in which the said particulate material comprises magnetically attractable material.

12. A reagent according to claim 10 which is in the form of a latex suspension.

13. A method of assaying a fluid by agglutination for an antigen therein, which comprises the steps of:
   (a) mixing a sample of the fluid with labelled F(ab')$_2$ fragments of an immunoglobulin which is specific to said antigen to form a reaction mixture, the labels being water-insoluble particles, wherein, to avoid interference from exogenous C1q and RF, the reaction is substantially free from the whole immunoglobulin and the F(c) fragments thereof;
   (b) incubating the mixture to allow a competition binding reaction between the F(ab')$_2$ fragments and any said antigen present;
   (c) analyzing the amount of labelled fragments which have reacted with the antigen or remain unreacted in the mixture to determine the presence and/or amount of antigen in the fluid.

* * * * *